(12) United States Patent
Moeller et al.

(10) Patent No.: US 9,435,775 B2
(45) Date of Patent: Sep. 6, 2016

(54) FLUID SWITCHING VALVE

(75) Inventors: Mark W. Moeller, Kingston, MA (US); Theodore D. Ciolkosz, Plymouth, MA (US)

(73) Assignee: Waters Technologies Corporation, Milford, MA (US)

( * ) Notice: Subject to any disclaimer, the term of this patent is extended or adjusted under 35 U.S.C. 154(b) by 307 days.

(21) Appl. No.: 13/980,380

(22) PCT Filed: Feb. 3, 2012

(86) PCT No.: PCT/US2012/023759
§ 371 (c)(1),
(2), (4) Date: Sep. 16, 2013

(87) PCT Pub. No.: WO2012/109103
PCT Pub. Date: Aug. 16, 2012

(65) Prior Publication Data
US 2014/0007660 A1    Jan. 9, 2014

Related U.S. Application Data

(60) Provisional application No. 61/440,013, filed on Feb. 7, 2011.

(51) Int. Cl.
  *G01N 1/00*   (2006.01)
  *G01N 30/38*  (2006.01)
  (Continued)

(52) U.S. Cl.
  CPC .............. *G01N 30/38* (2013.01); *F16K 11/10* (2013.01); *G01N 30/20* (2013.01); *G01N 2030/201* (2013.01); *G01N 2030/202* (2013.01); *G01N 2030/204* (2013.01); *Y10T 137/87909* (2015.04)

(58) Field of Classification Search
  CPC ....... G01N 30/32; G01N 30/34; G01N 30/20
  USPC ................................ 73/61.56; 251/205, 208
  See application file for complete search history.

U.S. PATENT DOCUMENTS 2,757,541 A    8/1956  Watson et al.
3,297,053 A    1/1967  McKinney
(Continued)

FOREIGN PATENT DOCUMENTS

WO    2009003519    1/2009

OTHER PUBLICATIONS

PCT International Search Report for PCT/US2012/023759, dated May 18, 2012, 4 pages.

(Continued)

*Primary Examiner* — Hezron E Williams
*Assistant Examiner* — Rodney T Frank
(74) *Attorney, Agent, or Firm* — Waters Technologies Corporation

(57) ABSTRACT

A fluid switching valve includes a first valve element (e.g., a stator) that has a plurality of first fluid-conveying features (e.g., ports), and a second valve element (e.g., a rotor) that has one or more second fluid-conveying features (e.g., fluid conduits in the form of grooves). The second valve element is movable, relative to the first valve element, between a plurality of discrete positions such that, in each of the discrete positions, at least one of the one or more second fluid-conveying features overlaps with multiple ones of the first fluid conveying features to provide for fluid communication therebetween. At least one of the first valve element and the second valve element includes a recess. The recess serves to reduce wear between the first valve element and the second valve element. The recess is arranged such that it does not overlap with any of the first fluid-conveying features or any of the second fluid-conveying features when the rotor is in any of the discrete positions.

19 Claims, 10 Drawing Sheets

(51) Int. Cl.
　　*G01N 30/20*　　(2006.01)
　　*F16K 11/10*　　(2006.01)

(56) References Cited

U.S. PATENT DOCUMENTS

| | | |
|---|---|---|
| 3,885,439 A | 5/1975 | Stone |
| 4,059,009 A | 11/1977 | Ball et al. |
| 4,444,066 A | 4/1984 | Ogle et al. |
| 4,506,558 A | 3/1985 | Bakalyar |
| 4,822,569 A | 4/1989 | Pellegrino |
| 5,419,208 A | 5/1995 | Schick |
| 6,012,487 A | 1/2000 | Hauck |
| 6,453,946 B2 | 9/2002 | Nichols et al. |
| 6,872,361 B2 | 3/2005 | Li et al. |
| 2006/0042686 A1 | 3/2006 | Gamache et al. |

OTHER PUBLICATIONS

PCT International Written Report for PCT/US2012/023759, dated May 18, 2012, 5 pages.

FLUID SWITCHING VALVE

RELATED APPLICATIONS

This application is a utility application claiming priority to U.S. Provisional Application Ser. No. 61/440,013, filed on Feb. 7, 2011, entitled "Fluid Switching Valve," the entirety of which is incorporated by reference herein.

TECHNICAL FIELD

This disclosure relates to fluid switching valves, such as fluid switching valves for chromatography systems.

BACKGROUND

Many analytic systems incorporate fluid switching valves for controlling fluid flow. An example is the use of rotary shear valves in some chromatography systems. In such chromatography systems, the rotary shear valves are typically employed for the purpose of introducing a sample (analyte) into a mobile phase stream (carrier fluid), which then carries the sample into a chromatography column.

Rotary shear valves generally consist of a rotor and a stator, which seal and wear against each other. The rotor, which is typically a softer wearing part, rotates against the stator, which is typically a harder part that exhibits less wear. As a consequence of the rotation of the rotor against the mating stator, it is common for material to begin to wear off the rotor. The wear rate of the rotor is often not uniform, since travel distance (a main contributor to wear) is based on distance from the center of rotor and angular movement. The resulting wear differences can reduce the operational life of the valve.

SUMMARY

In one aspect, a fluid switching valve includes a first valve element (e.g., a stator) that has a plurality of first fluid-conveying features (e.g., ports), and a second valve element (e.g., a rotor) that has one or more second fluid-conveying features (e.g., fluid conduits in the form of grooves). The second valve element is movable, relative to the first valve element, between a plurality of discrete positions such that, in each of the discrete positions, at least one of the one or more second fluid-conveying features overlaps with multiple ones of the first fluid conveying features to provide for fluid communication therebetween. At least one of the first valve element and the second valve element includes a recess. The recess serves to reduce wear between the first valve element and the second valve element. The recess is arranged such that it does not overlap with any of the first fluid-conveying features or any of the second fluid-conveying features when the rotor is in any of the discrete positions.

According to another aspect, a rotary shear valve includes a stator that has two or more ports, and a rotor that has a fluid conduit and a recess. The rotor is movable, relative to the stator, between at least two positions. In one of the positions, the fluid conduit is disposed to allow fluid to flow from a first one of the ports to a second one of the ports, and, in another one of the positions, the fluid conduit does not permit fluid flow between the first one of the ports and the second one of the ports. The recess is not connectable with any of the ports or the fluid conduit in any position of the rotor relative to the stator.

Implementations can include one or more of the following features.

In some implementations, the recess is positioned such that particles worn from the first valve element or the second valve element collect within the recess when the second valve element is moved relative to the first valve element.

In certain implementations, the second valve element includes a plurality of second fluid-conveying features and the recess. The recess is arranged such that the distance between any part of the recess and any of the second fluid-conveying features is not shorter than the shortest distance between any of the second fluid-conveying features.

The first valve element can include the recess, and the recess can be arranged such that the distance between any part of the recess and any of the first fluid-conveying features is not shorter than the shortest distance between any of the first fluid-conveying features.

In some implementations, the recess is arranged in a region in which the travel of the second valve element relative to the first valve element is greatest.

In certain implementations, the recess is disposed about an axis of rotation of the second valve element.

In some cases, the fluid switching valve is a slide valve in which the second valve element is linearly displaceable relative to the first valve element to move between the plurality of discrete positions.

In some implementations, the second valve element is rotatable, relative to the first valve element, to move between the plurality of discrete positions. For example, the fluid switching valve can be a rotary shear valve in which the first valve element comprises a stator and the second valve element comprises a rotor. Alternatively, the fluid switching valve can be a cylindrical valve in which the first valve element comprises a tubular outer member and the second valve member comprises a rotatable cylindrical inner member.

In some implementations, the valve is incorporated in a chromatography system (e.g., a gas or liquid chromatography system). The chromatography system can include a chromatography column in fluid communication with the valve. The valve can be arranged to control a flow of a mobile phase stream to the chromatography column.

The valve can be configured for use with liquid flows of between about 0.01 and 10 mL/minute and at max pressures between about 5000 and 20000 psi.

The recess can be positioned proximate to the periphery of the rotor where the travel of the rotor relative to the stator is greatest.

In some implementations, the rotor has a greater diameter than the stator, and the recess is positioned selected such that a part of the recess is outside the periphery of the stator.

In certain implementations, the rotor rotates about an axis passing through its center, and wherein the recess is positioned at the center of the rotor.

Implementations can include one or more of the following advantages.

In some implementations, fluid switching valves are provided which have extended lifetimes in comparison with prior types of valve having similar function.

Other aspects, features, and advantages are in the description, drawings, and claims.

DETAILED DESCRIPTION

A fluid switching valve can be provided with one or more relief areas (e.g., recesses) to help to reduce wear differences occurring between valve elements and thereby extending the operating life of the fluid switch valve.

Figure 1:
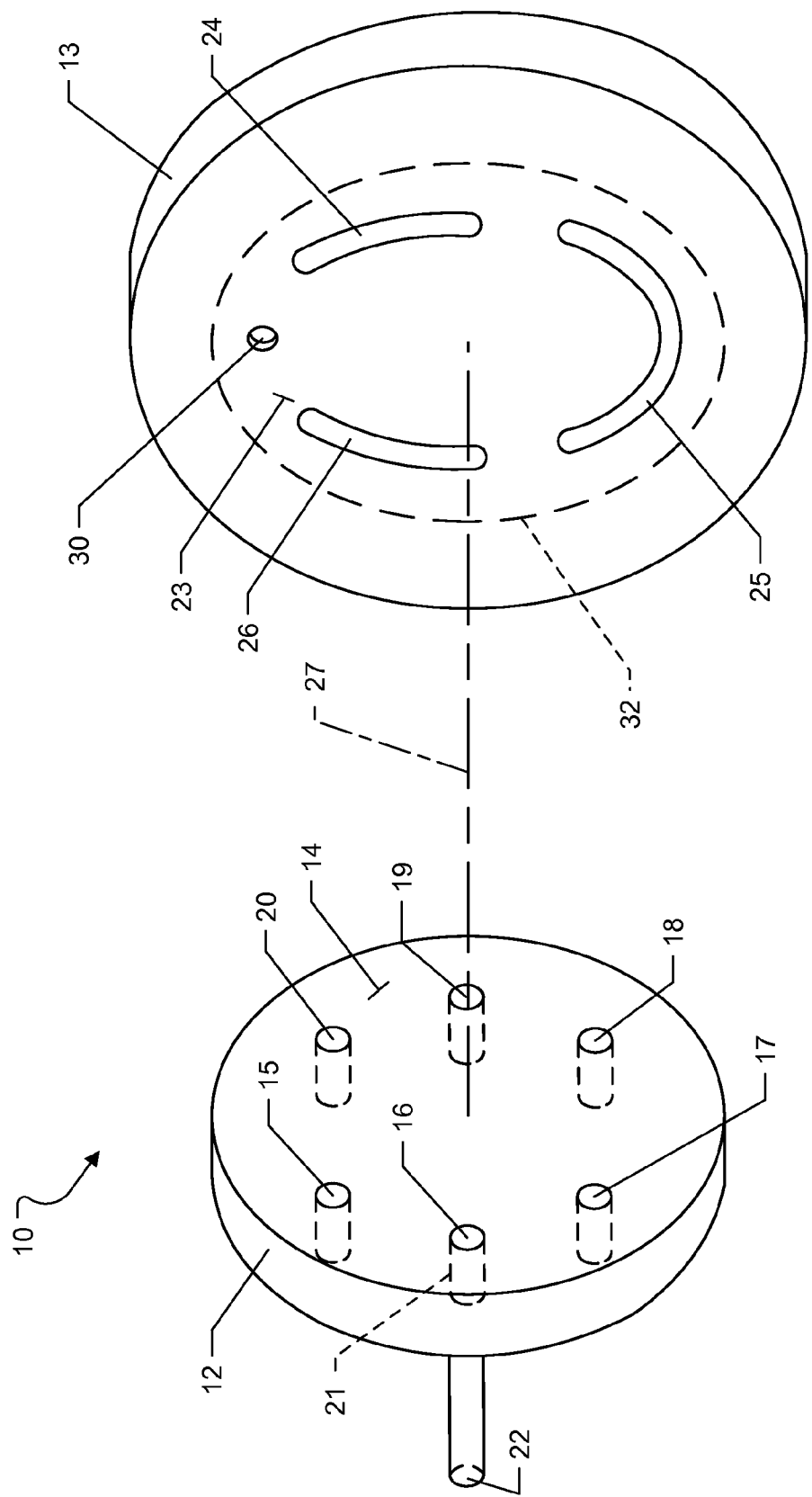
FIG. 1 is an exploded perspective view of a rotary shear valve that includes a rotor having a recess for collecting wear particles.

Referring to FIG. 1, a six-port rotary shear valve 10 includes a stator 12 and a larger diameter rotor 13. The stator 12 has a stator interface 14 and a plurality of ports 2-7. Each of ports 2-7 includes a passage (shown at 21 in the case of the port 16) which connects the port on the stator interface 14 to the rear of the stator 12. Fluid connections to the ports 15-20 can then be made to the various ports via the passages (e.g., the pipe 22 in the case of passage 21). The connection can include a socket formed in the stator 12 for receiving a ferrule fitted to the pipe and a suitable securing nut, as in the case of a conventional pipe union.

The ports 15-20 can be approximately 0.006 inches diameter and can be arranged in a circular array of diameter 0.1 inches. The external diameter of the stator 12 can be about 0.15 inches. The stator 12 can be manufactured from stainless steel, or other corrosion resistant alloy. The stator interface 14 can be coated with a wear resistant material, for example diamond-like carbon (DLC).

The rotor 13 has a rotor interface 23, which includes three fluid conduits 24, 25, 26 in the form of arcuate grooves, which link pairs of adjacent ports 15-20. When assembled, the rotor interface 23 is urged into contact with the stator interface 14, e.g., by pressure exerted on the rotor 13 by a spring, to help ensure a fluid-tight seal therebetween. The rotor 13 is capable of rotation about an axis 27 and has two discrete positions relative to the stator 12. In a first position, groove 24 overlaps and connects ports 15 and 16, groove 25 overlaps and connects ports 17 and 18, and groove 26 overlaps and connects ports 19 and 20. In the second position, groove 24 overlaps and connects ports 16 and 17, groove 25 overlaps and connects ports 18 and 19, and groove 26 overlaps and connects ports 20 and 15.

Notably, the rotor 13 is provided with a relief area in the form of a recess 30 that is disposed close to, but wholly within a boundary 32 of the periphery of the stator 12 when the stator 12 is in position adjacent the rotor 13. The recess 30 serves to collect wear particles generated by repeated operation of the valve 10. These wear particles can remain in the recess 30 as the rotor 13 turns relative to the stator 12. The collection of wear particles helps to remove the wear particles away from the rotor interface 23 and the mating stator interface 14 where the wear particles might otherwise accumulate and interfere with sealing and/or contribute to non-uniform wear between the rotor 13 and the stator 12. As a result the recess 30 can help to extend the operating life of the valve 10.

The recess 30 can be positioned relative to the fluid conduits 24-26 in such a way as to maximize the distance between the recess 30 and any part of the fluid conduits 24-26. In some cases, the distance is not significantly less than the distance between the fluid conduits 24-26 themselves so that risk of fluid leakage from the fluid conduits 24-26 between the stator interface 14 and the rotor interface 23 is not increased.

The position of recess 30 can be further selected so that, as the valve is operated, the recess 30 tracks over a region where the greatest wear is likely to take place. In the case of a rotary shear valve, the region of greatest wear is often close to the periphery of the smaller of the stator and rotor, because a point on the periphery will travel the greatest distance as the valve is operated, causing the greatest amount of wear.

The recess 30 can be circular and of approximately the same diameter as the width of the fluid conduits 24-26 so that the same tool can be used to machine both the recess 30 and the fluid conduits 24-26 during manufacture of the rotor 13. The diameter of the rotor 13 is about 0.200 inches. The fluid conduits 24-26 can consist of 0.008 inch wide by 0.008 inch deep arcuate grooves extending for 60°, spaced apart along a circular path of the same diameter of the array of ports (0.1 inches). The recess 30 can be about 0.008 inches to about 0.016 inches diameter and 0.01 inches deep. The rotor 13 can be manufactured from polyether-ether-ketone, such as PEEK™ polymer (available from Victrex PLC, Lancashire, United Kingdom), filled with between 20 and 50% carbon fiber. Alternatively or additionally, the rotor 13 can be manufactured from polyimide (available as DuPont™ VESPEL® polyimide from E. I. du Pont de Nemours and Company), or polyphenylene sulfide (PPS).

Figure 2A:
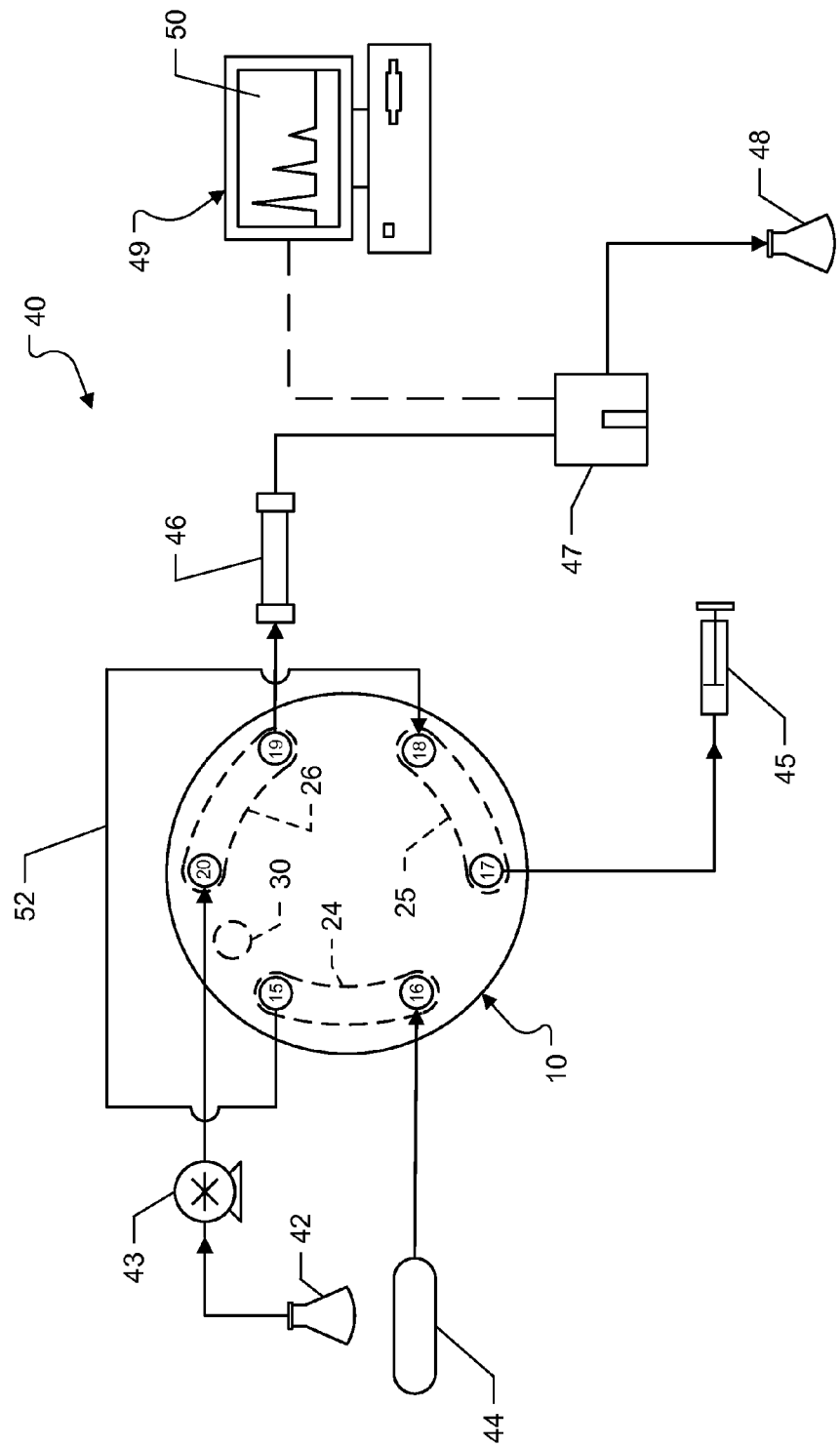
FIGS. 2A and 2B are schematic views of a high performance liquid chromatography system including the rotary shear valve of FIG. 1.
Figure 2B:
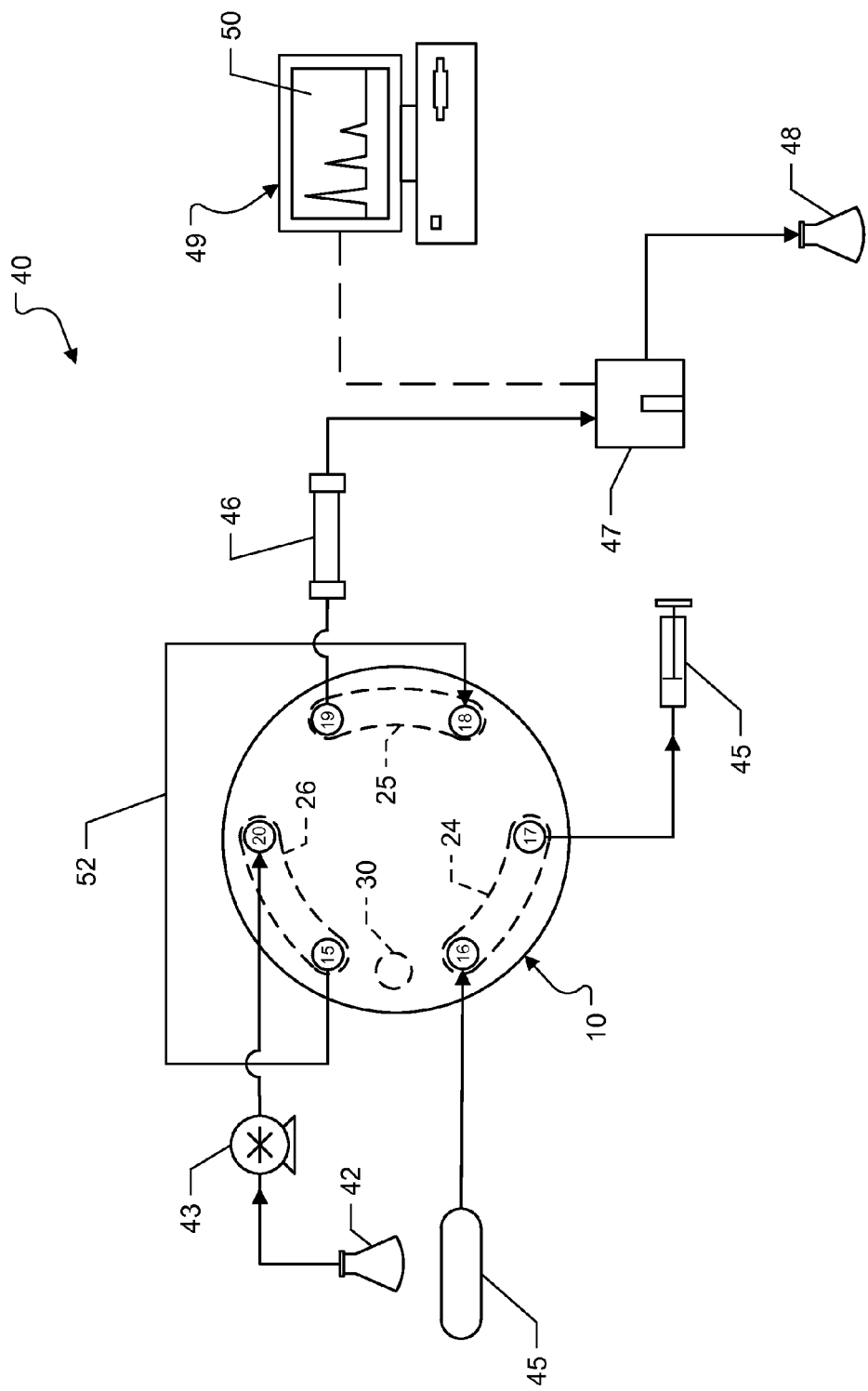

A valve with this configuration can be used for injecting samples into the flow of a fluid for subsequent chromatographic analysis, both for gas chromatography and for liquid chromatography. For example, FIGS. 2A and 2B illustrate a high performance liquid chromatography (HPLC) system 40 that incorporates the six-port rotary shear valve 10 of FIG. 1. Referring to FIGS. 2A and 2B, a carrier fluid reservoir 42 holds a carrier fluid. A carrier fluid pump 43 is used to generate and meter a specified flow rate of the carrier fluid, typically milliliters per minute. The carrier fluid pump 43 delivers the carrier fluid to the valve 10. A sample, from a sample source 44 (e.g., a sample vial), is introduced into the valve 10 where it can combine with the flow of carrier fluid, which then carries the sample into a chromatography column 46. In this regard, the sample may be aspirated from the sample source 44 through the action of an aspirator 45 (e.g., a syringe assembly). A detector 47 is employed to detect separated compound bands as they elute from the chromatography column 46. The carrier fluid exits the detector 47 and can be sent to waste 48, or collected, as desired. The detector 47 is wired to a computer data station 49, which records an electrical signal that is used to generate a chromatogram on its display 50.

In use, when the valve 10 is in a first position (FIG. 2A), port 15 is in fluid communication with port 16, port 17 is in fluid communication with port 18, and port 19 is in fluid communication with port 20. In this first position, the sample flows into the valve 10 via port 16 and then into a sample loop 52 (e.g., a hollow tube) via port 15, and carrier fluid is delivered into the valve 10 via port 20 and then toward the chromatography column 46 and the detector 47 via port 19.

When the valve's rotor is rotated into a second position (FIG. 2B), port 15 is placed in fluid communication with port 20, port 16 is placed in fluid communication with port 17, and port 18 is placed in fluid communication with port 19. In this second position, the carrier fluid is conveyed through the sample loop 52, where it merges with the sample, and then carries the sample downstream to the chromatography column 46 and the detector 47.

For ultra high performance liquid chromatography, the valve 10 may have to operate at very high pressures (up to 20,000 psi in some cases). The valve 10 may also have to have minimal dead volume and very low leak rates, given that the flow rates at which it operates in the HPLC system 40 can be as low as 1 or 2 ml/min. Consequently, the pressure applied to the rotor 13 (FIG. 1) may be as high as 22,000 psi in order to obtain a seal of sufficient quality between the rotor 13 and the stator 12 (FIG. 1). As a result, the rotor 13 and/or stator 12 may begin to wear, which could adversely affect the performance and operating life of the valve. However, the recess 30 helps to collect wear particles generated by repeated operation of the valve 10. These wear particles remain in the recess 30 as the rotor 13 turns relative to the stator 12, thereby inhibiting (e.g., preventing) the wear particles from becoming trapped between the rotor 13 and the stator 12 and contributing to further damage to the rotor 13 and/or the stator 12. As a result, the lifetime of the valve can be increased and system downtime for repair and/or replacement of the valve can be reduced.

Other Implementations

Figure 3:
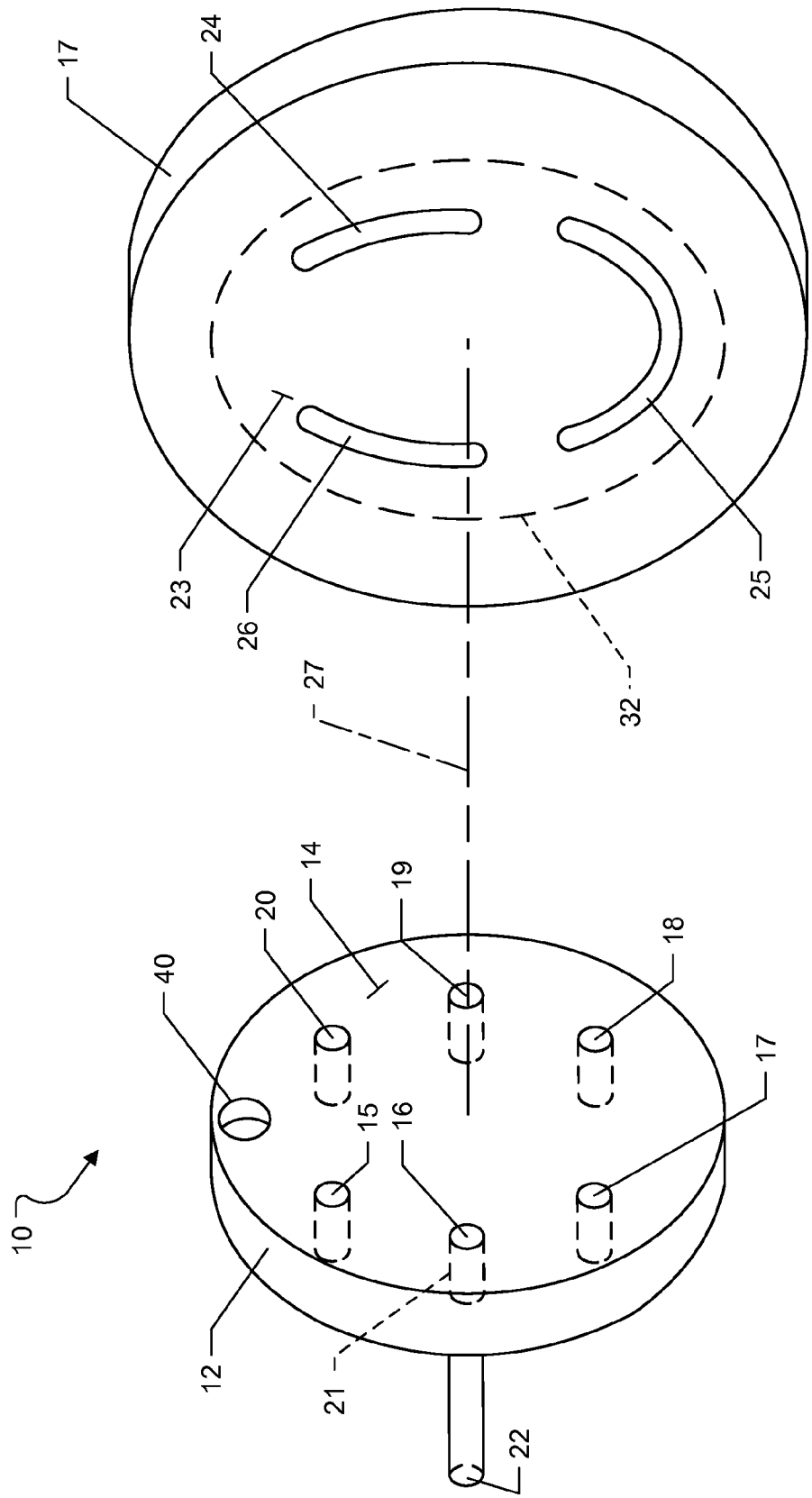
FIG. 3 is an exploded perspective view of a rotary shear valve that includes a stator having a recess for collecting wear particles.

Although certain implementations have been described in detail above, other modifications are possible. For example, although an implementation has been described in which a recess is formed in a rotor, one or more recesses 60 can, alternatively or additionally, be provided in the stator 12, as shown in FIG. 3.

Figure 4:
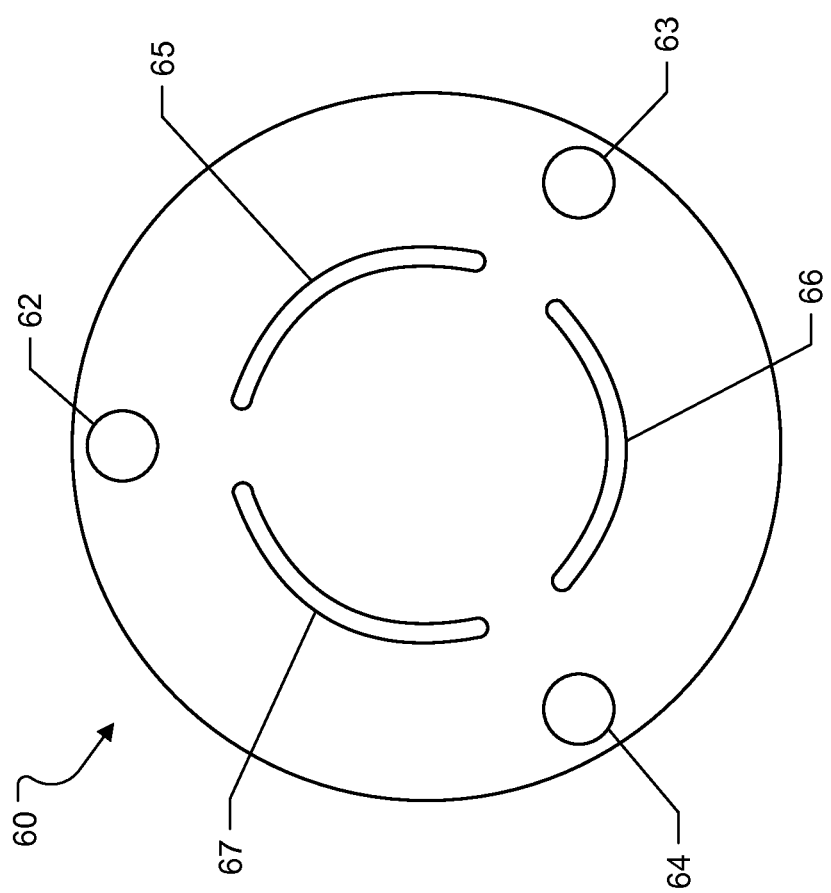
FIG. 4 is a plan view of a rotor, for a rotary shear valve, having a plurality of recesses for collecting wear particles.

In some implementations, more than one recess can be provided to collect wear particles at different parts of the rotor. For example, FIG. 4 shows a rotor 70 having three recesses 72, 73, and 74 for collecting wear particles as well as three fluid conduits 75, 66, and 77. Provision of more than one recess is useful when extent of rotation of the valve is limited, in which case a single recess in the rotor will travel only over a portion of the stator. The area of contact of the first and second surfaces is also further reduced by such provision.

Figure 5A:
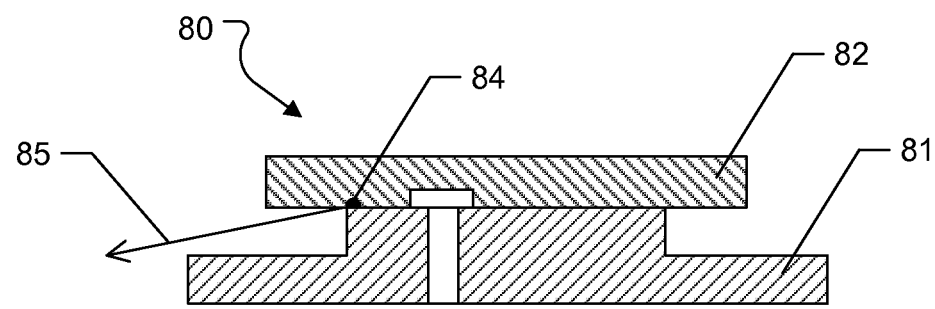
FIG. 5A is a sectional view of a rotary shear valve that has not been used.
Figure 5B:
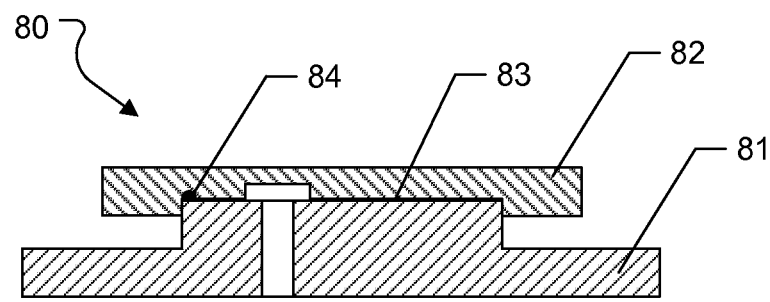
FIG. 5B is a sectional view of the rotary shear valve of FIG. 5A after extensive use.
Figure 5C:
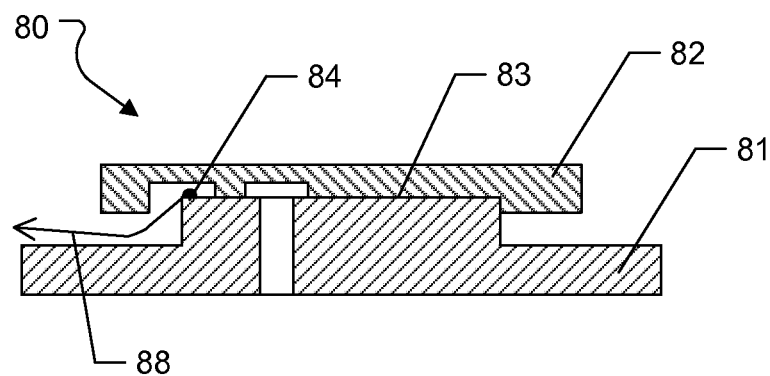
FIG. 5C is a sectional view a rotary shear valve having a recess positioned to reduce accumulation of wear particles.

In some implementations, a rotary sheer valve can include a rotor having a recess that overlaps an edge of a mating stator. Such an arrangement can allow wear particles to be ejected from between the mating interfaces of the rotor and stator, and, as a result the operating life of the rotary sheer valve can be extended. FIG. 5A shows a simplified sectional drawing through a new (unused) rotary sheer valve 80 including a stator 81 and a rotor 82, while FIG. 5B shows the same valve 80 in which the rotor 82 is significantly worn through repeated cycles of operation. In the worn valve (FIG. 5B), a central portion 83 of the rotor 82 in contact with the stator 81 has been reduced in thickness due to the wear, causing an outer (unworn) portion of the rotor to overlap the periphery of the stator 81. In the case of the new valve (FIG. 5A) it can be seen that a particle 84 produced by wear close to the periphery of the stator 81 is likely to be ejected from the valve as indicated by the arrow 85, so that it will not cause further damage. However, in the case of the worn valve shown in FIG. 5B, the wear particle 84 is prevented from leaving the valve by the overlapping portion of the rotor 82, and its presence is likely to result in further damage to the valve 80. In order to minimize this problem, the rotor 82 can be provided with a recess 86 that overlaps an edge 87 of the stator 81, as shown in FIG. 5C. As the rotor 82 turns on the stator 81, wear particles formed close to the edge 87 can be collected in the recess 86 and can be ejected from the valve as indicated by the arrow 88.

In the case of a valve of similar dimension to that described above with regard to FIG. 1, the recess 86 can be approximately 0.012 inches×0.020 inches and be approximately 0.010 inches deep.

Figure 6:
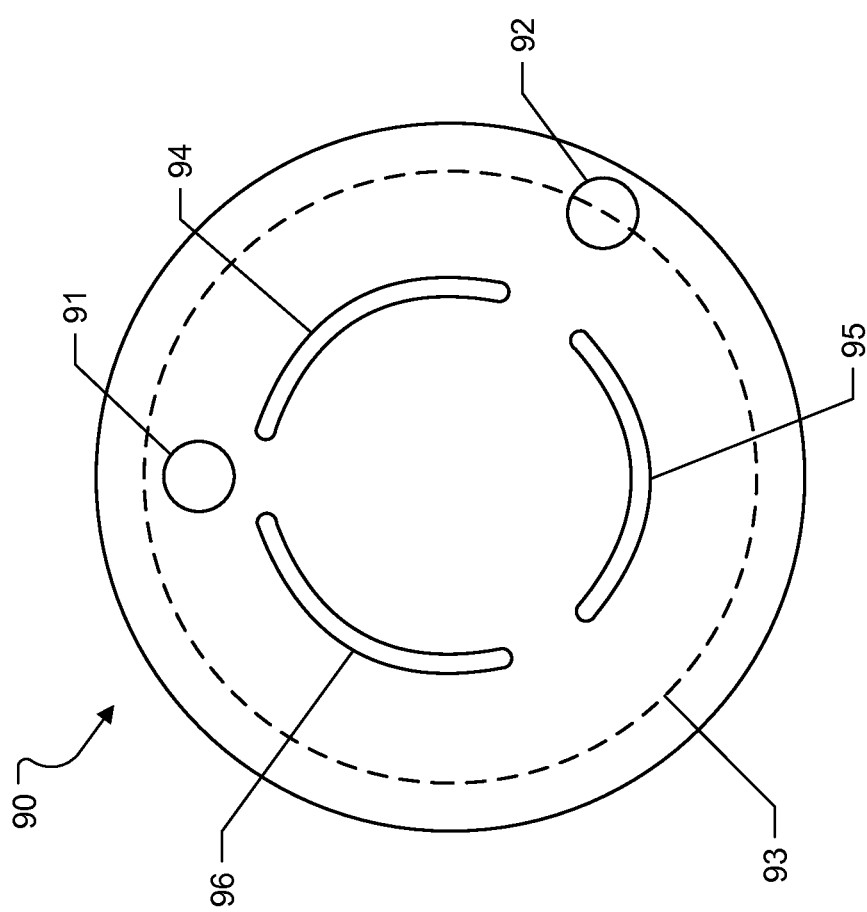
FIG. 6 is a plan view of a rotor, for a rotary shear valve, having a plurality of recesses including a recess positioned to reduce accumulation of wear particles.

In some implementations, more than one recess can be provided in a rotor of a shear valve. For example, FIG. 6 shows a rotor 90 that includes a recess 91 similar to recess 30 of FIG. 1, and a recess 92 similar to the recess 86 shown in FIG. 5C. The position of the periphery of a mating stator, when the valve is assembled, is shown at 93. The rotor 90 also includes fluid conduits 94, 95, and 96. Both recesses 91 and 92 can be positioned as far as practical from the fluid conduits 94, 95, and 96 to avoid compromising the leak rate of the valve.

Figure 7:
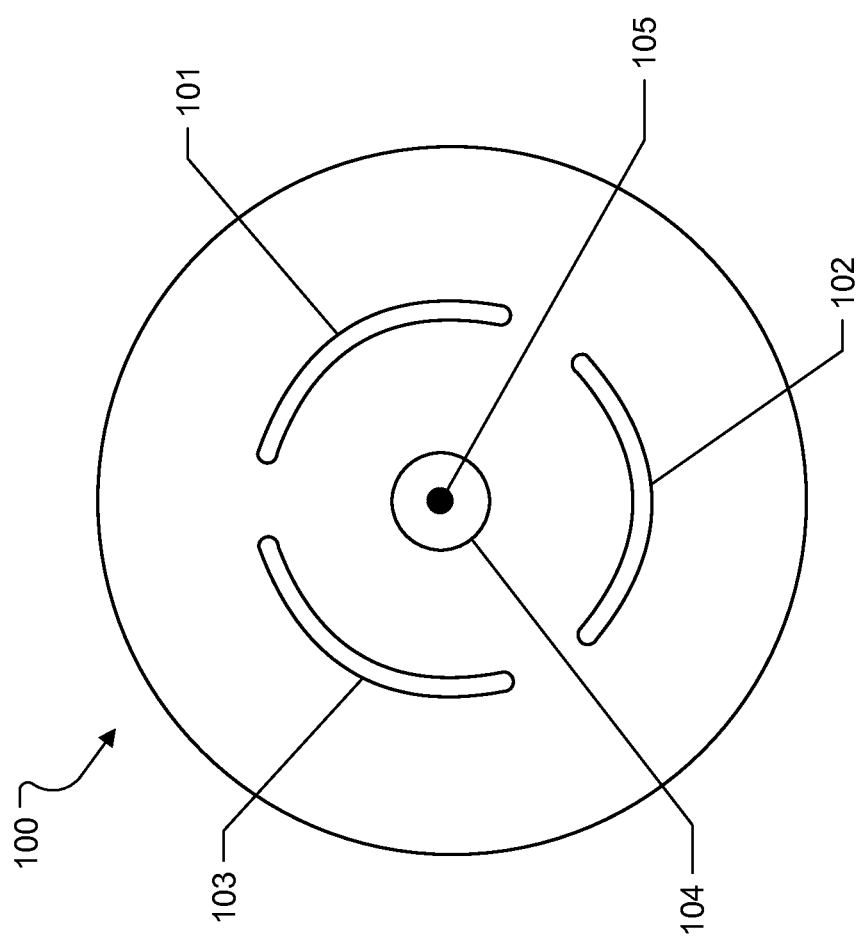
FIG. 7 is a plan view of a rotor, for a rotary shear valve, having a recess positioned about its axis of rotation.

In some implementations, a recess can be provided along the axis of rotation of a rotor. Such a recess can be provided on the rotor, on a mating, or both. As an example, FIG. 7 shows a rotor 100 that includes three fluid conduits 101, 102, and 103, and has a recess 104 disposed about its axis of rotation 105.

The inventors have observed that there is often less wear in the center of a rotor (or stator) than at its periphery. This can inhibit the worn portion closer to the periphery from contacting the stator, thus degrading the seal between the two components. Provision of a recess in either the rotor or the stator on the axis of rotation alleviates this effect and increases the lifetime of the valve, and also allows particles to collect at the centre of the rotor, preventing it causing further damage. The recess can be provided additionally or alternatively to the recesses previously described. On the case of the valve dimensioned as described, the recess 104 can be about 0.016 inches diameter and 0.010 inches deep.

Figure 8:
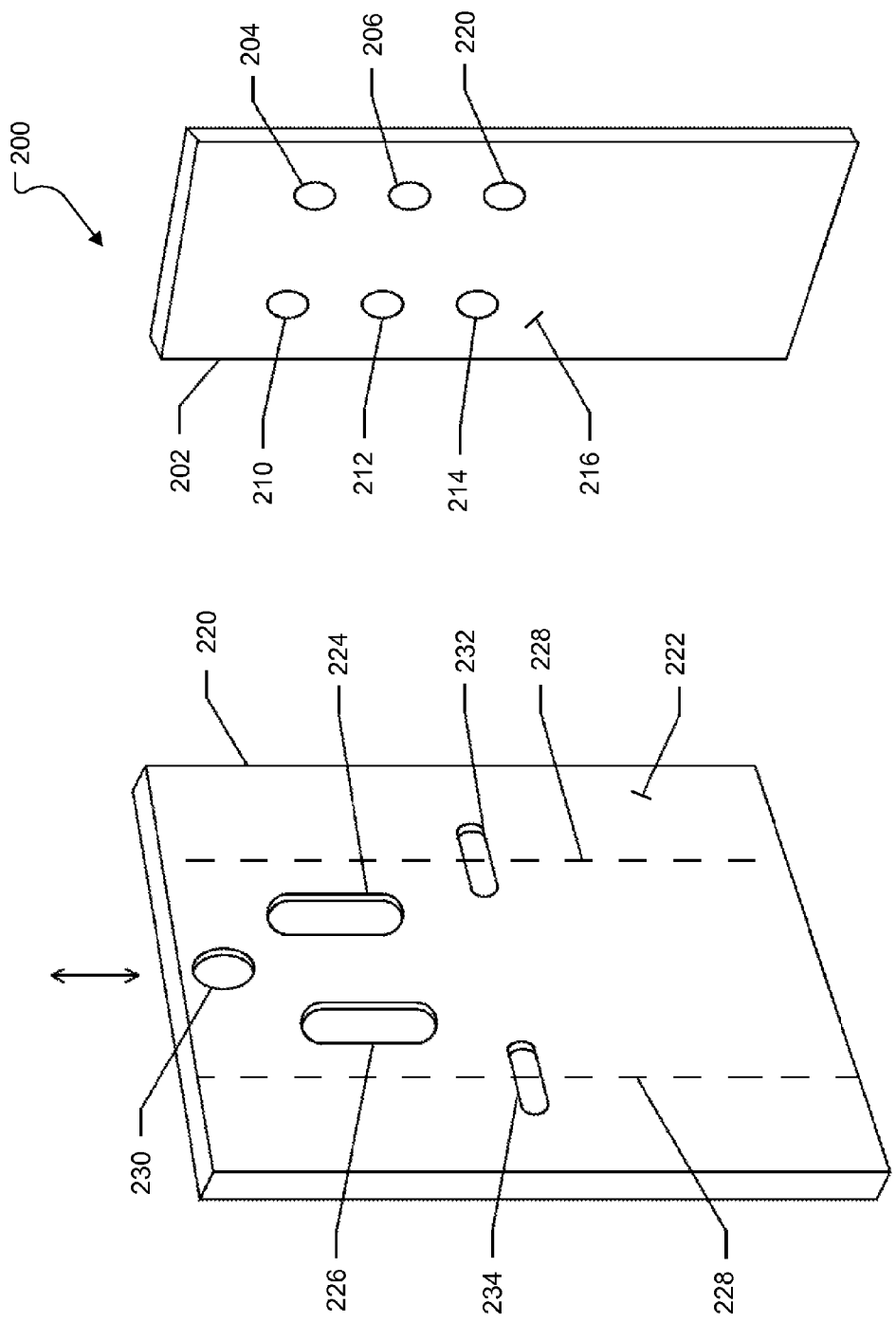
FIG. 8 is an exploded perspective view of a slide valve that includes recesses for accommodating wear particles.

Another implementation provides a slide valve in which a first valve element slides laterally across a second valve element as opposed to rotating on an axis. Such a valve 200 is illustrated in FIG. 8, and can include a fixed member 202 and a slidable member 220. The fixed member 202 comprises 6 ports 204, 206, 208, 210, 212, and 214 in its fixed member interface 216. These ports can be connected to pipe work for conveying fluid to and from the ports. The slidable member 220 can comprise a slidable member interface 222 and two fluid conduits 224 and 226 in the form of short linear grooves in the slidable member interface 222. In use, the fixed member interface 216 and the slidable member interface 222 are maintained in sealing contact with one another. In a first position of the slidable member 220 relative to the fixed member 202, the fluid conduit 224 is disposed to allow fluid to flow between ports 210 and 212, while fluid conduit 226 allows fluid to flow between ports 204 and 206. In a second position of the slidable member 220 relative to the fixed member 202, fluid conduit 224 permits fluid flow between ports 212 and 214, while fluid conduit 226 permits fluid flow between ports 206 and 208. The dotted lines 228 indicate the position of the fixed member 202 relative the slidable member 220 when the valve 200 is assembled. Conveniently, the fixed member 202 is manufactured from stainless steel, or other corrosion resistant alloy, and the slidable member 220 is manufactured from a carbon-filled PEEK™, PPS, or polyimide. Consequently, the slidable member 220 can wear with repeated operation of the valve, generating wear particles. In this regard, one or more recesses 230 can be provided in the slidable member 220 and/or the fixed member 202 in order to collect the wear particles and prevent them from causing further damage. For example, a recess 230 can be provided close to the center line of the valve 220 to collect wear particles generated in this region. Recesses 232 and 234, disposed along the lines 228, can also be provided. These recesses 232 and 234 overlap the edges of the fixed member 202 and can allow wear particles to escape from the valve 200, as does the recess 86 in the case of the valve shown in FIG. 5C.

Figure 9:
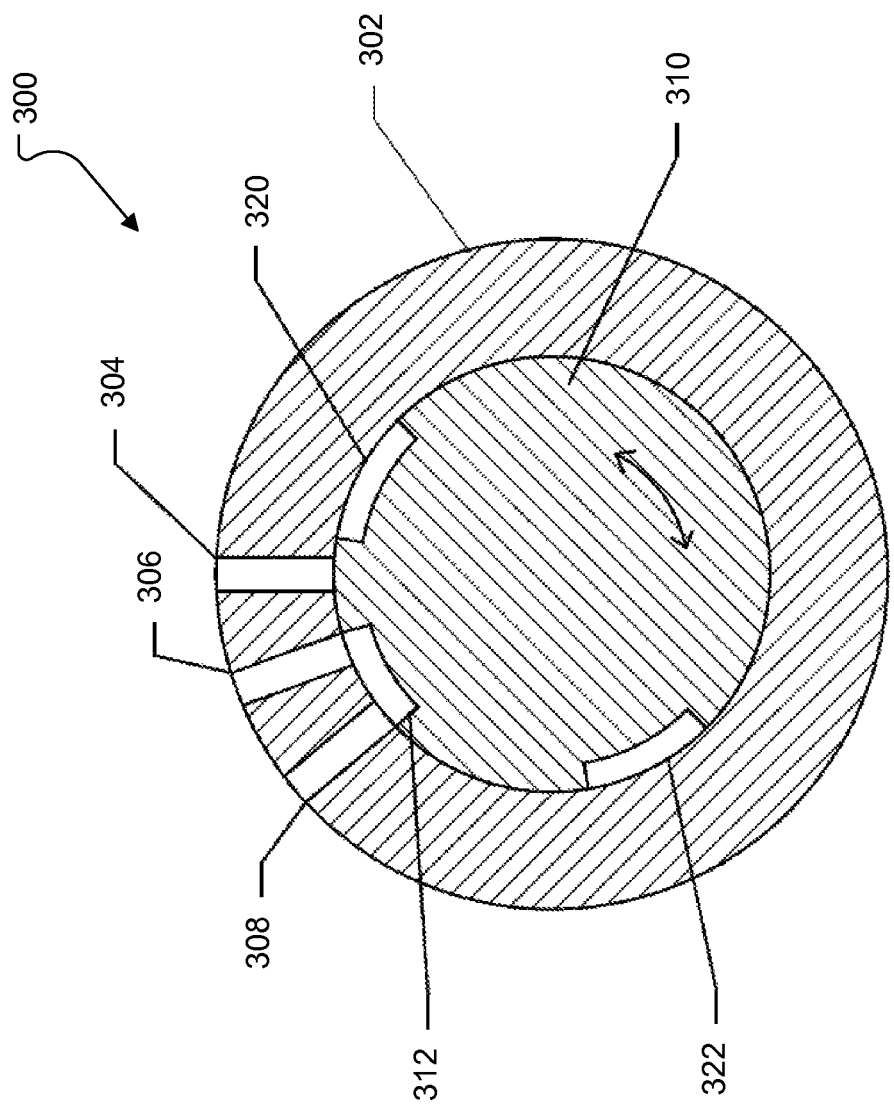
FIG. 9 is a sectional view of a cylindrical valve that includes recesses for accommodating wear particles.

FIG. 9 illustrates a cylindrical valve 300. A tubular outer member 302 having an annular cross-section can be manufactured from stainless steel, or other corrosion resistant alloy, and can include a number of ports 304, 306, and 308. A rotatable cylindrical inner member 310 is disposed within the tubular outer member 302 and includes a fluid conduit 312 in the form of a passage. The inner member 310 can be rotated so that the fluid conduit 312 connects ports 304 and 306, or ports 306 and 308, depending on its position relative to the outer member 302 Inner member 310 can be manufactured from a carbon-filled PEEK™, PPS, or polyimide and its outer surface is such as to provide a fluid-tight seal with the bore of the tubular outer member 302. This implementation can provide one or more recesses 320 and 322 in the outer surface of the inner member 310, not connectable with any of the ports 304, 306, and 308. Recesses 320 and 322 can collect wear particles, preventing them from becoming trapped between the sealing surfaces of the inner and outer members where they can cause further damage and degrade the life time of the valve.

Another implementation can provide a cylindrical valve in which the inner member slides along its axis in order to provide a connection between the ports, rather than rotating as in the case of the valve shown in FIG. 9. Such a valve can comprise recesses in the outer surface of the inner member for collecting wear particles for collecting wear particles. These recesses can be arranged according to the principles outlined above.

Accordingly, other implementations are within the scope of the following claims.

What is claimed is:

1. A fluid switching valve comprising:
   a first valve element having a plurality of first fluid-conveying features;
   a second valve element having one or more second fluid-conveying features,
   wherein the second valve element is movable, relative to the first valve element, between a plurality of discrete positions such that, in each of the discrete positions, at least one of the one or more second fluid-conveying features overlaps with multiple ones of the first fluid conveying features to provide for fluid communication therebetween, and
   wherein at least one of the first valve element and the second valve element includes a recess, the recess serving to reduce wear between the first valve element and the second valve element and arranged such that it does not overlap with any of the first fluid-conveying features or any of the second fluid-conveying features when the rotor is in any of the discrete positions.

2. The fluid switching valve of claim 1, wherein the recess is positioned such that particles worn from the first valve element or the second valve element collect within the recess when the second valve element is moved relative to the first valve element.

3. The fluid switching valve of claim 1, wherein the second valve element includes a plurality of second fluid-conveying features and the recess, and wherein the recess is arranged such that the distance between any part of the recess and any of the second fluid-conveying features is not shorter than the shortest distance between any of the second fluid-conveying features.

4. The fluid switching valve of claim 1, wherein the first valve element includes the recess, and wherein the recess is arranged such that the distance between any part of the recess and any of the first fluid-conveying features is not shorter than the shortest distance between any of the first fluid-conveying features.

5. The fluid switching valve of claim 1, wherein the recess is arranged in a region in which the travel of the second valve element relative to the first valve element is greatest.

6. The fluid switching valve of claim 1, wherein the recess is disposed about an axis of rotation of the second valve element.

7. The fluid switching valve of claim 1, wherein the fluid switching valve is a slide valve in which the second valve element is linearly displaceable relative to the first valve element to move between the plurality of discrete positions.

8. The fluid switching valve of claim 1, wherein the second valve element is rotatable, relative to the first valve element, to move between the plurality of discrete positions.

9. The fluid switching valve of claim 8, wherein the fluid switching valve is a rotary shear valve in which the first valve element comprises a stator and the second valve element comprises a rotor.

10. The fluid switching valve of claim 8, wherein the fluid switching valve is a cylindrical valve in which the first valve element comprises a tubular outer member and the second valve member comprises a rotatable cylindrical inner member.

11. The fluid switching valve of claim 1, wherein the first fluid-conveying features comprise ports.

12. The fluid switching valve of claim 1, wherein the second fluid-conveying features comprise grooves.

13. A chromatography system comprising the fluid switching valve of claim 1 and a chromatography column in fluid communication with the fluid switching valve, wherein the fluid switching valve is operable to control a flow of a mobile phase stream to the chromatography column.

14. The chromatography system of claim 13, wherein the fluid switching valve is configured for use with liquid flows of between about 0.01 and 10 mL/minute and at pressures between about 5000 and 20000 psi.

15. A rotary shear valve comprising:
   a stator having two or more ports; and
   a rotor having a fluid conduit and a recess,
   wherein the rotor is movable, relative to the stator, between at least two positions,
   wherein in one of the positions, the fluid conduit is disposed to allow fluid to flow from a first one of the ports to a second one of the ports, and, in another one of the positions, the fluid conduit does not permit fluid flow between the first one of the ports and the second one of the ports, and
   wherein the recess is not connectable with any of the ports or the fluid conduit in any position of the rotor relative to the stator.

16. The rotary shear valve of claim 15, wherein the valve is configured for use with liquid flows of between about 0.01 and 10 mL/minute and at pressures between about 5000 and 20000 psi.

17. The rotary shear valve of claim 15, wherein the recess is positioned proximate to the periphery of the rotor where the travel of the rotor relative to the stator is greatest.

18. The rotary shear valve of claim 15, wherein the rotor has a greater diameter than the stator, and wherein the recess is positioned selected such that a part of the recess is outside the periphery of the stator.

19. The rotary shear valve of claim 15, wherein the rotor rotates about an axis passing through its center, and wherein the recess is positioned at the center of the rotor.

* * * * *